United States Patent [19]
Obel et al.

[11] Patent Number: 5,865,838
[45] Date of Patent: Feb. 2, 1999

[54] LOW ENERGY IMPLANTABLE ATRIAL DEFIBRILLATOR USING MULTIPLE ELECTRODES AND STIMULATION RATES

[75] Inventors: Martin Obel, Danderyd; Sven-Erik Hedberg, Kungsängen, both of Sweden

[73] Assignee: Pacesetter AB, Järfalla, Sweden

[21] Appl. No.: 932,653

[22] Filed: Sep. 18, 1997

[30] Foreign Application Priority Data

Aug. 16, 1996 [SE] Sweden .................................. 9603000

[51] Int. Cl.$^6$ ...................................................... A61N 1/39
[52] U.S. Cl. .................................. 607/5; 607/14; 607/15
[58] Field of Search ................................ 607/5, 9, 14, 15

[56] References Cited

U.S. PATENT DOCUMENTS

| | | |
|---|---|---|
| 5,161,528 | 11/1992 | Sweeney . |
| 5,209,229 | 5/1993 | Gilli ............................................ 607/5 |
| 5,403,356 | 4/1995 | Hill et al. ................................... 607/14 |
| 5,433,729 | 7/1995 | Adams et al. . |
| 5,464,433 | 11/1995 | White et al. . |
| 5,490,862 | 2/1996 | Adams et al. . |
| 5,683,429 | 11/1997 | Mehra ....................................... 607/14 |

FOREIGN PATENT DOCUMENTS

WO 95/28987 11/1995 WIPO .............................. A61N 1/39

Primary Examiner—William E. Kamm
Assistant Examiner—Carl H. Layno
Attorney, Agent, or Firm—Hill & Simpson

[57] ABSTRACT

In an apparatus for terminating atrial fibrillation using pulses having an energy content which is the same as the energy content of conventional pacing pulses, stimulation pulses are respectively emitted by a number of electrodes disposed at different sites in or on a heart experiencing atrial fibrillation. When atrial fibrillation is detected, waveforms are measured at each of the electrodes, and the electrode having the waveform exhibiting the shortest interval between successive identifiable, cyclical waveform characteristics, such as successive P-waves, is selected as a first electrode for beginning an atrial defibrillation attempt. Stimulation pulses are emitted from the first electrode at a stimulation rate which is slightly shorter than the aforementioned shortest interval and the other electrodes are stimulated at a rate which is slightly shorter than the rate for the first electrode. All of the stimulation pulses are delivered starting at the latest local detection point in time. Upon each of the other electrodes reaching a point at which emits a stimulation pulse which coincides with a stimulation pulse emitted by the first electrode, that other electrode is locked to the stimulation rate of the first electrode, until all of the electrodes are stimulating at a coincident rate. Detection is periodically undertaken to determine whether atrial fibrillation has been terminated, and if so the pacemaker resumes its normal pacing operation. If the atrial fibrillation has not been terminated, the procedure is continued (if not yet ended) or repeated.

9 Claims, 3 Drawing Sheets

LOW ENERGY IMPLANTABLE ATRIAL DEFIBRILLATOR USING MULTIPLE ELECTRODES AND STIMULATION RATES

BACKGROUND OF THE INVENTION

1. Field of the Invention

The present invention is directed to an apparatus for treating atrial fibrillation, and in particular to an apparatus for doing so by means of multi-site pacing.

2. Description of the Prior Art

A healthy heart functions to pump blood through the circulatory system in successive, periodic cycles each including an atrial contraction followed shortly thereafter by a ventricular contraction. The successive atrial and ventricular contractions occur upon being triggered by the heart's natural pacemaker, which causes electrical wavefronts to propagate through cardiac tissue, causing the tissue cells to be momentarily polarized, thereby causing the contractions. If a patient's natural pacemaker, through disease, ceases to function or functions only erratically, artificial pacing therapy can be provided by an implanted pacemaker, which delivers low-energy pacing pulses to the atrium, or to the ventricle, or to both the atrium and the ventricle in a properly synchronized sequence. Depending on the needs of a particular patient, the pacemaker can be operated to continuously supply such pacing pulses without interruption, or can operate to sense when the patient's natural pacemaker has failed to deliver a signal resulting in contraction, and only then does the implanted pacemaker deliver a pacing pulse. Pacemakers of this latter type are known as demand pacemakers.

Fibrillation, in general, characterizes abnormal operation of the heart, which can spontaneously occur, wherein the normal propagation of the electrical wavefronts becomes chaotic and therefore the cardiac tissue never receives a clear or coherent signal triggering contraction, and pumping therefore ceases. Ventricular fibrillation is a life-threatening condition, and when it occurs must be treated rapidly and effectively. For this purpose, implantable defibrillators are well-known in the art, which deliver one or more high-energy electrical pulses to the cardiac tissue, at selected locations and in a selected timing sequence, so as to momentarily depolarize substantially all of the cardiac tissue, thereby rendering virtually all of the cardiac tissue momentarily unable to propagate the chaotic wavefronts. If defibrillation is successful, when the cells again become capable of propagating a pacing wavefront, they will do so in a normal, non-chaotic manner.

Atrial fibrillation is usually not a life-threatening pathology, and can be tolerated for a certain amount of time without significant adverse consequences to the patient. This means that upon the occurrence of atrial fibrillation, there is usually a relatively long time during which an effective therapy can be developed, and subsequently administered. Although implantable defibrillator technology, primarily intended for treating ventricular fibrillation, can be adapted also to treat atrial fibrillation, the delivery of high energy shocks to the patient is painful and moreover, such drastic therapy is usually not necessary in the case of atrial fibrillation. Atrial fibrillation is also treated by extracorporeal delivery of the shocks to the heart through the skin of the patient by an external defibrillator of the type well-known in the art, also being extremely uncomfortable for the patient. Moreover, this type of treatment generally results only in temporary relief for patients, and must be repeated.

In treating atrial fibrillation by means of electrical shocks supplied to the heart, such shocks must be applied in synchronism with the ventricular electrical activity otherwise ventricular fibrillation may be induced.

Another treatment regimen for atrial fibrillation is the administration of suitable drugs for reducing the occurrences of atrial fibrillation. Drugs suitable for this purpose which are currently available, however, have many undesirable side effects, and many patients become resistant to their atrial fibrillation suppressing properties, thereby significantly reducing the therapeutic effect of such drugs.

Another type of cardiac arrhythmia is tachycardia, which is a condition whereby the heart's natural pacemaker begins to cause contractions at an abnormally rapid rate. In many instances, tachycardia can be treated by administering pulses at the same energy content as normal pacing pulses, but the anti-tachycardia pulses are delivered in a particular sequence which is designed to return the heart to its normal pacing rate. A conventional cardiac pacemaker, however, has only one pacing electrode disposed in electrical contact with atrial tissue and/or one pacing electrode disposed in electrical contact with ventricular tissue. Administration of pulses having an energy comparable to pacing pulse energy, at a single site in the atrium, has never been shown to terminate atrial fibrillation.

The reason why single site pacing has not been successful in terminating atrial fibrillation is that atrial fibrillation is characterized by the existence of several propagation wavefronts. It has been shown that pacing at one site in the atrium will influence wavefront loops only within a region having a diameter of approximately three centimeters around the pacing site. Since the other propagation loops are thus unaffected by pulses applied to this single site, it has not been possible to terminate atrial fibrillation by supplying such pulses only to one site. Many articles have been published regarding ventricular fibrillation which state that a condition for successful termination of ventricular fibrillation is to ensure that no wavefront loop, or only one wavefront loop, remains after administration of the defibrillation therapy. Atrial fibrillation is similar to ventricular fibrillation, and the same conditions should apply for the successful termination of atrial fibrillation.

SUMMARY OF THE INVENTION

It is an object of the present invention to provide an apparatus for terminating atrial fibrillation without causing pain to the patient.

It is a further object of the present invention to provide an apparatus for terminating atrial fibrillation by the delivery of pulses to the heart having an energy content which is substantially the same as the energy content of conventional pacing pulses, e.g., 0.5 joules or less.

This object is achieved in accordance with the principles of the present invention in an apparatus having a number of electrodes respectively placed at multiple sites in contact with atrial tissue, with stimulation pulses being delivered in individual sequences by the electrodes, the sequences being monitored and controlled so as to eventually all become coincident with pulses emitted at a pulse interval which is set dependent on a measured or estimated interval between peaks in the atrial fibrillation cycle which is being treated.

The electrodes used for the multi-site pacing may be endocardial and/or epicardial electrodes. The electrodes are stimulated independently of each other, but in a timing sequence which is set in accordance with the principles of the present invention. The spacing of the electrodes from each other is on the order of the size of the wavefront loop area.

A number of different stimulation patterns and electrode positions can be used in accordance with the invention. The timing of the stimulation pulses at one site should be closely coupled to the refractory period of the atrial cells at this site. This time can be estimated from measurements obtained before the beginning of atrial fibrillation, or during atrial fibrillation. It is known that the atrial refractory period may decrease if atrial fibrillation persists. The time duration over which this decrease takes place is on the order of tens of hours. This must be taken into consideration if the atrial refractory period is only estimated, rather than actually measured. Techniques used to determine refractory periods when the patient is not experiencing atrial fibrillation will be similar to established electrophysiologic procedures. If, however, atrial fibrillation already exists when the estimation of the refractory period is undertaken, the time interval between each detected electrical pulse at each site will determine, in accordance with the invention, the interval to be used for the terminating attempt.

The terminating attempt in accordance with the invention proceeds as follows. It is first determined from which of the several electrodes at the respective sites having the shortest time interval between atrial activity waveform. The P-wave interval can be used for this purpose. The electrode which is identified as having the shortest interval associated therewith is then used as the electrode from which a first stimulation pulse sequence is emitted in the termination attempt. The measured or estimated interval must be on the order of the refractory period of the atrial cells, or longer. If the interval is too long, the detection may be due to cross-detection, and another electrode site should then be selected, which most likely has the true shortest interval. The first stimuli in a termination attempt are delivered just before the next anticipated spontaneous activity will occur. This takes place at every electrode site.

The first stimulation pulse controls the timing of the other stimulation pulses, with the pulse intervals associated with other electrodes being gradually reduced so that they will eventually coincide with the timing of the first electrode. As soon as one electrode reaches this condition of equality of the interval between successive pulses, the pulses emitted by that electrode are locked to the pulse sequence of the first electrode so that all subsequent pulses will be emitted at the same time as the pulses emitted by the first electrode. This procedure continues until all electrodes are caused to deliver all pulses at the same time.

The interval between the pulses, by virtue of the above procedure, is now slightly longer than the refractory period of the atrial cells. This condition may not exist for long, and different post termination procedures may then follow. In one example, the intervals will gradually be longer. If there was a successful termination of the atrial fibrillation, the atrial pacing rate will then be synchronized to the stimuli. If the termination attempt is unsuccessful, the procedure should be repeated. Since the original termination attempt, however, may have changed the atrial fibrillation pattern, it is necessary to undertake a new measurement or estimation of the fibrillation characteristics before the next termination attempt is begun.

Another manner of ending the termination attempt is to stop the delivery of pulses to the electrodes when the emission pulses from all of the electrodes has been synchronized for a predetermined or programmable number of pulses.

The atrial electrodes can be located at many different positions on or in the heart, bearing in mind that the distance between electrodes should be on the order of approximately three centimeters, for the reasons mentioned above. Electrodes may be placed in both atria for delivering the terminating stimuli. Another possibility is to position electrodes in the coronary sinus. Epicardial or endocardial electrode placement can be used exclusively, or epicardial and endocardial placement can be used in combination.

DESCRIPTION OF THE PREFERRED EMBODIMENTS

Figure 1:
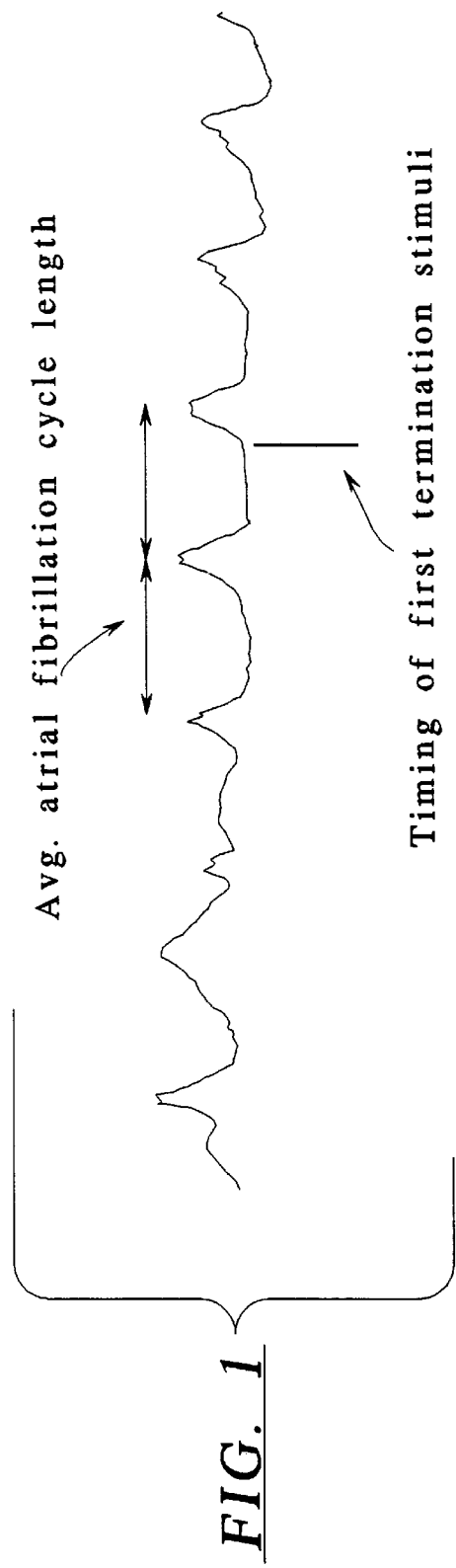
FIG. 1 shows an atrial IECG signal with an indication of the chronological position at which first termination stimuli are emitted in accordance with an exemplary embodiment of the invention.

A typical IECG waveform of the type obtained from a patient experiencing atrial fibrillation is shown in FIG. 1. As can be seen, this waveform consists of a number of successive peaks, each peak constituting an end of a previous atrial fibrillation cycle and the beginning of the next atrial fibrillation cycle. Since the true maximum of each peak usually cannot be identified with precision, an average cycle length must be determined or estimated, as shown in FIG. 1. In accordance with the principles of the present invention, a waveform of the type shown in FIG. 1 is obtained from each location on or in a heart experiencing atrial fibrillation, using multi-site electrodes respectively connected to detection circuitry. The electrode from which a waveform is measured which has the shortest cycle length is used as the electrode to emit a first pulse, or series of pulses, in an atrial fibrillation termination attempt. As also explained in more detail below, the first stimuli in an attempt are delivered just before the next anticipated spontaneous activity, as indicated in FIG. 1.

Figure 2:
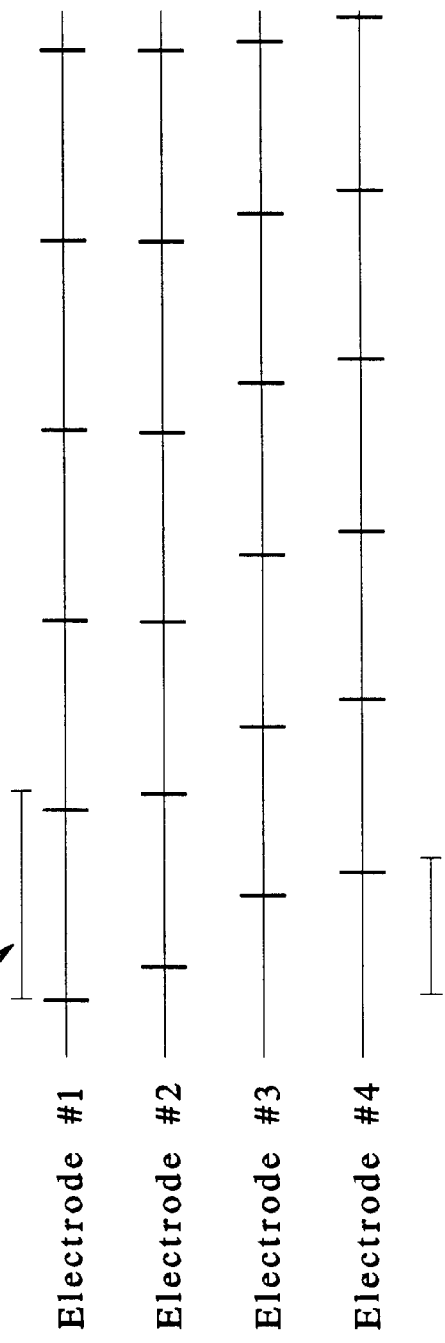
FIG. 2 illustrates the manner by which the stimuli emitted by the respective electrodes at multiple sites become synchronized in accordance with the principles of the present invention.

FIG. 2 shows how the timing of the other stimuli becomes synchronized with the emission of the first-delivered stimuli. The electrode from which the firstdelivered stimuli were emitted is designated as electrode #1 in FIG. 2, and the remaining electrodes are designated in sequence. In the exemplary embodiment shown in FIG. 2, there are three other electrodes, designated electrode #2, electrode #3 and electrode #4, for a total of four multi-site electrodes. More or fewer electrodes, however, can be used without departing from the principles of the present invention. As can be seen in FIG. 2, and as explained in detail in the flow chart shown in FIG. 4, the first stimulation pulse emitted by electrode #1 in FIG. 1 controls the timing of the other stimuli delivered by the other electrodes. As soon as any one of electrode #2, electrode #3 or electrode #4 emits a pulse coinciding with the emission of a pulse from the electrode which has been designated as electrode #1, that electrode is thereafter caused to continue to emit pulses coinciding with the emission of pulses from electrode #1. This continues until all electrodes deliver pulses at the same time. The time over which all of the respective pulse intervals of the other electrodes come to coincide will vary, and it will likely be a longer time than the intervals indicated in the exemplary embodiment shown in FIG. 2, for explanatory purposes. Although FIG. 2 shows, for explanatory purposes, pulse emission coincidence occurs in sequence from electrode #2 to electrode #3 to electrode #4, but this is only because the electrodes are numerically designated in FIG. 2 in the sequence in which they come to deliver pulses coinciding with the pulses from electrode #1. In actual practice, there is no numerical pre-designation of any of the electrodes; whichever electrode has the shortest interval becomes designated, in the control program, as electrode #1, and as the other electrodes successively begin to emit pulses coinciding with the timing of the pulses from electrode #1, those electrodes become respectively numbered as electrode #2, electrode #3, etc. in the control program.

When all of the multi-site electrodes have reached a point at which they emit stimuli synchronized with the stimuli emitted by electrode #1, the interval between the pulses will be slightly longer than the refractory period of the atrial cells, and it must then be considered if and when to terminate the atrial defibrillation attempt. If it is determined at this time that the termination attempt has been successful, conventional atrial pacing can then be resumed, synchronized with the stimulation rate which successfully terminated the atrial fibrillation. If it is determined that the attempt was unsuccessful, the entire procedure should be repeated, however, in the repeated attempt and in any repeated attempts which may follow, the previous termination attempt may have changed the atrial fibrillation pattern, and therefore a new observation of the fibrillation characteristics should be undertaken before beginning the next attempt.

Alternatively, termination of the attempt can be programmed to take place when all of the pulses have been synchronized for a predetermined or programmed number of pulses.

Figure 3:
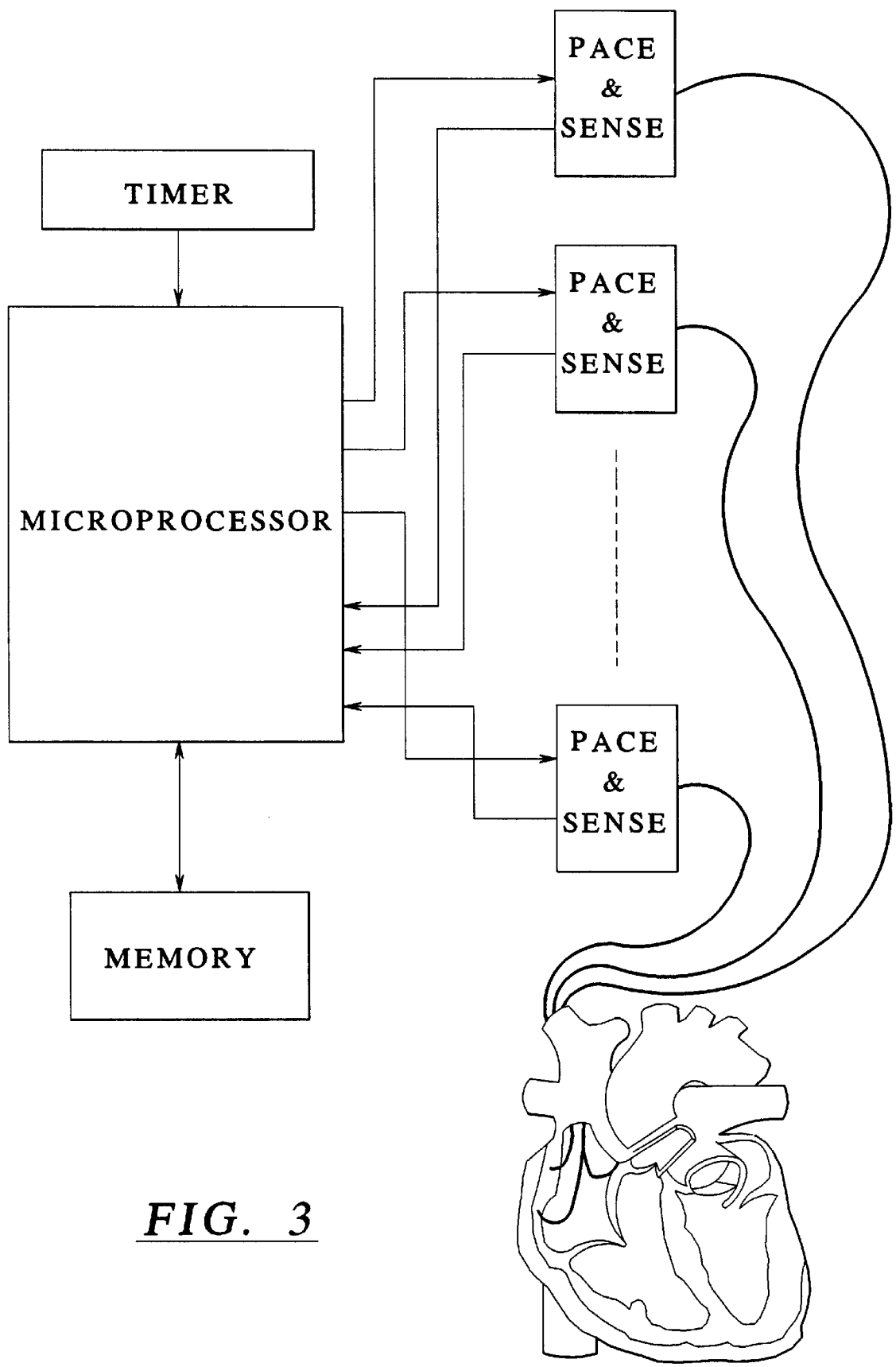
FIG. 3 shows an exemplary apparatus for terminating atrial fibrillation, constructed in accordance with the principles of the present invention.

FIG. 3 shows a schematic block diagram of an implantable cardiac pacemaker, connected in vivo to a heart, operable in the manner described above for terminating atrial fibrillation. In the embodiment shown in FIG. 3, three electrode cables, each terminating in an electrode at respectively different sites in the heart, are used, however, as explained above, more electrodes can alternatively be used. It is also possible to arrange two or more electrodes on one electrode cable. In the embodiment of FIG. 3, the electrode tips are shown as terminating in the right atrium, however, electrodes may alternatively be placed in the left atrium, or in both atria. Also, in the exemplary embodiment of FIG. 3 endocardial leads are shown, however, epicardial leads may alternatively be used, as well as a combination of endocardial and epicardial leads.

Each lead is connected in a known manner to the connector of an implantable pacemaker having a housing (not shown) serving as the indifferent electrode. Within the pacemaker housing, each lead proceeds via an electrical connection to its own pace and sense unit, which serves as a schematic representation of all of the known circuitry which is commonly used for the generation and delivery of pacing pulses, and the sensing of cardiac activity. Each pace and sense unit has an output supplied to a microprocessor within the pacemaker housing, and also receives an output from the microprocessor. The microprocessor controls the sensing and pacing which takes place in each pace and sense unit. The microprocessor is operated by a software program stored in a memory and by a timer, which supplies information to the microprocessor as to when stimulation pulses are to be delivered. The timer may be set by the microprocessor for proper timing of the stimulation pulses. Although not shown in FIG. 3, the microprocessor and/or the memory can be in telemetric communication with an external programmer, by means of which the program can be altered, or parameters set, and also by means of which data can be read from the memory.

Figure 4:
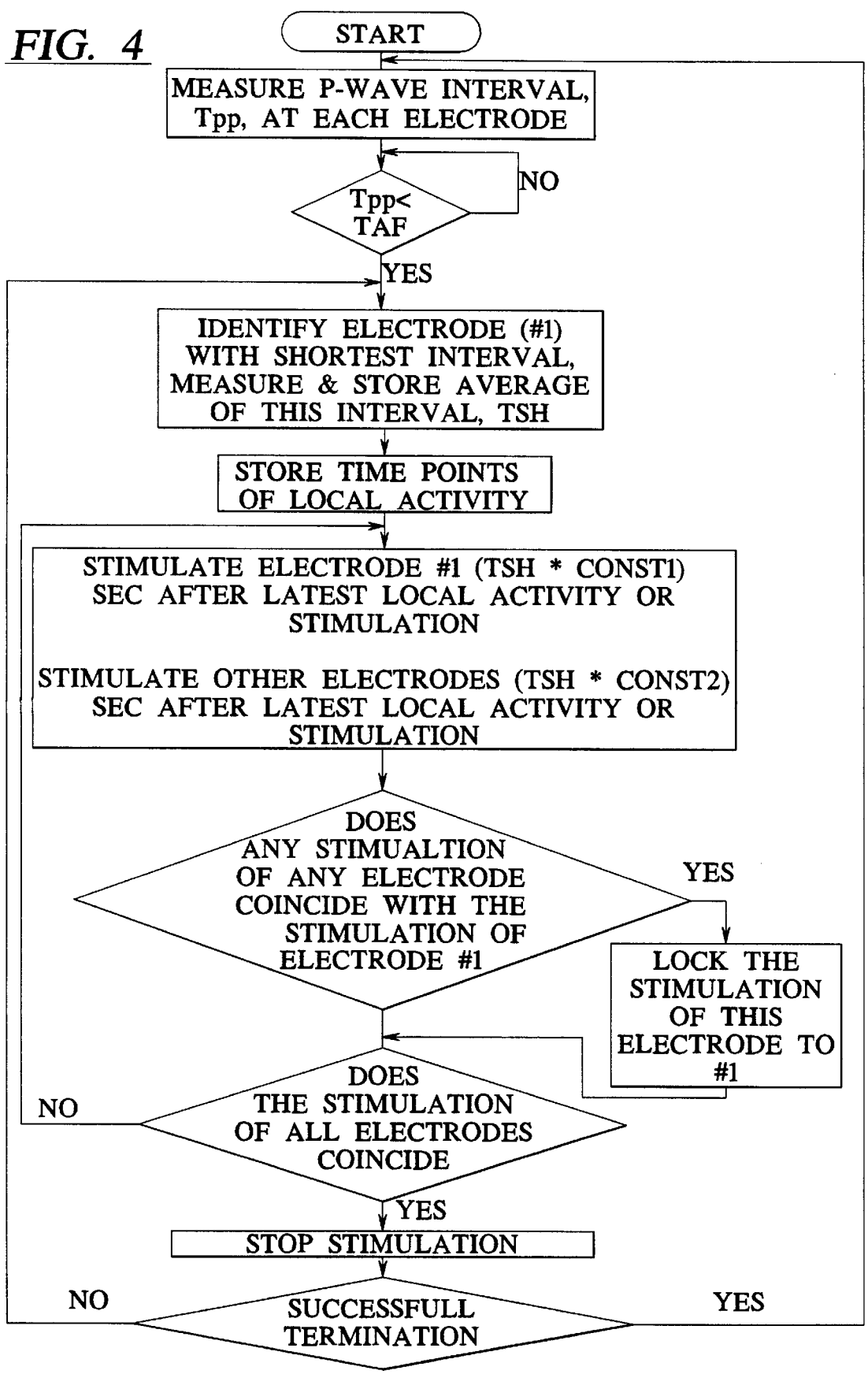
FIG. 4 is a flow chart showing the basic steps in the inventive procedure for terminating atrial fibrillation.

The atrial fibrillation termination procedure outlined above is shown in more detail in the flow chart of FIG. 4. The pacemaker is normally in a "detect atrial arrhythmia" loop. If and when atrial fibrillation is detected, which is preferably accomplished by observing the P-wave interval $T_{pp}$ and determining if it is shorter than a set interval $T_{AF}$, the shortest interval between atrial activation pulses at each electrode position is measured and stored in the memory of FIG. 3. An average value of these intervals must be obtained, since normally there is a variation among these intervals which cannot be ignored. The electrode at which the waveform was measured having the shortest interval $T_{SH}$ is then designated as electrode #1, and is used to start termination of the atrial fibrillation. The stimulation interval at this point is set at a somewhat shorter interval than the shortest loop interval which has been measured. This stimulation interval may be obtained, for example, by multiplying $T_{SH}$ by a constant CONST1, which may be approximately 0.95–0.99. Stimulation pulses are supplied to the other electrodes with an interval between pulses which is slightly shorter than the stimulation interval for electrode #1. The interval for these other electrodes may be obtained, for example, by multiplying the shortest loop interval $T_{sh}$ by a different constant, CONST2, which may be on the order of 0.95×CONST1. All of the stimulation pulses are delivered with the respective intervals beginning at the latest local detection point in time. This means that the other stimulation pulses will gradually move closer to the stimulation pulses emitted by electrode #1. After the emission of a number of stimuli, which depends on the phase relation between the individual pacing at each electrode, the stimulation pulses, if the attempt is successful, will become synchronized more closely, and will finally coincide. As soon as the stimulation pulses from one of the other electrodes coincide with the pulses emitted by electrode #1, that electrode stimulation rate is then locked to the rate of the stimulation pulses emitted by electrode #1. If these stimulation pulses have been able to control the atrial wavefront loop in the vicinity of that electrode, the atrial fibrillation may have been terminated. A check to determine if termination was successful can be made by returning to the atrial fibrillation detection routine each time one more electrode comes into coincidence with electrode #1. If the procedure continues until all of the stimulation pulses for all of the electrodes coincide, the stimulation fibrillation termination mode can be stopped after the emission of a predetermined or programmable number of pulses are emitted in synchronization. If the result of this detection loop indicates that the termination has failed, the same procedure will be repeated. If the termination was successful, normal pacemaker operation is resumed.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an implantable apparatus for terminating atrial fibrillation having at least one electrode cable, with at least two electrodes placeable in electrical contact with atrial tissue, and said electrodes being placed at respectively different locations relative to a heart atrium, a pulse generator connected to each of said electrodes for emitting stimulation pulses via said electrodes with an energy of 0.5 joules or less, a detector connected to each electrode for sensing a waveform representing atrial activity at the site of the electrode, a microprocessor connected to the pulse generators and to the detectors for controlling delivery of said stimulation pulses and for analyzing detected atrial activity to identify the occurrence of atrial fibrillation of said heart, the improvement comprising means in said microprocessor for controlling delivery of said stimulation pulses in an attempt to terminate said atrial fibrillation, comprising:

means, upon detection of atrial fibrillation, for identifying one of said electrodes having a detected waveform with a shortest interval between a repeated, identifiable waveform characteristic, said one of said electrodes being designated as a first electrode;

means for supplying said stimulation pulses having an energy of 0.5 joules or less to said heart via said first electrode at a first electrode stimulation interval which is shorter than said shortest interval and for supplying stimulation pulses to the other electrodes at a different stimulation rate which is shorter than said first electrode stimulation rate, the stimulation pulses emitted by said first electrode and by said other electrodes all being delivered at intervals starting with a latest local detection point in time;

means for identifying when a stimulation pulse emitted by any of said other electrodes coincides with a stimulation pulse emitted by said first electrode and thereafter locking the stimulation rate of that electrode to said first electrode stimulation rate, until all stimulation pulses emitted by all of said electrodes coincide; and means for determining whether said atrial fibrillation has been terminated each time one of said other electrodes becomes locked to said first electrode and, if atrial fibrillation still exists for continuing said atrial defibrillation attempt until all electrodes are locked to said first electrode.

2. The implantable apparatus of claim 1 comprising means for setting said first electrode stimulation interval at a value which is the product of a constant multiplied by said shortest interval.

3. An implantable apparatus as claimed in claim 2 wherein said constant is in a range from 0.95 to 0.99.

4. An implantable apparatus as claimed in claim 1 comprising means for setting said other intervals at a value which is a product of a constant multiplied by said shortest interval.

5. An implantable apparatus as claimed in claim 1 comprising means for setting said first stimulation interval to a value which is a product of a first constant multiplied by said shortest interval, and means for setting said other intervals at a value which is a product of a second constant multiplied by said shortest interval.

6. An implantable apparatus as claimed in claim 5 wherein said second constant comprises a fraction of said first constant.

7. An implantable apparatus as claimed in claim 6 wherein said first constant is in a range from 0.95 to 0.99, and wherein said second constant is equal to a product of 0.95 multiplied by said first constant.

8. An implantable apparatus as claimed in claim 1 further comprising means for pacing said heart with said stimulation pulses having an energy of 0.5 joules or less at times when said atrial defibrillation attempt is not being executed.

9. An implantable apparatus as claimed in claim 1 wherein said means for identifying one of said electrodes having a shortest interval comprises means for identifying one of said electrodes having a shortest average P-wave interval in said waveform.

\* \* \* \* \*